United States Patent [19]

Böttcher et al.

[11] 4,164,873
[45] Aug. 21, 1979

[54] METHOD OF AND DEVICE FOR MATERIAL CHECKING BY ULTRA SOUND WHILE EMPLOYING AN ELECTRODYNAMIC SOUND CONVERTER

[75] Inventors: Wolfgang Böttcher; Hermann-Josef Kopineck, both of Dortmund, Fed. Rep. of Germany

[73] Assignee: Hoesch Werke Aktiengesellschaft, Dortmund, Fed. Rep. of Germany

[21] Appl. No.: 836,964

[22] Filed: Sep. 27, 1977

[30] Foreign Application Priority Data

Sep. 28, 1976 [DE] Fed. Rep. of Germany ....... 2643601

[51] Int. Cl.² .............................................. G01N 29/04
[52] U.S. Cl. ...................................................... 73/643
[58] Field of Search ................. 73/643, 627, 629, 620, 73/622; 324/226, 227, 232, 234, 238; 310/15

[56] References Cited

U.S. PATENT DOCUMENTS 3,583,213  6/1971  Houck ............................... 73/643 X
3,850,028  11/1974  Thompson et al. ..................... 73/643

Primary Examiner—Charles A. Ruehl
Attorney, Agent, or Firm—Becker & Becker

[57] ABSTRACT

A method of and device for ultrasonically checking a workpiece while employing an electrodynamic sound converter including a checking head and a coil adapted to be energized to create a magnetic field, according to which during the checking operation the workpiece in a continuous movement relatively is passed by the testing or checking head of the electrodynamic sound converter. The coil for generating the magnetic field is energized by an alternating current or an intermittent or alternating direct current. Furthermore, the electrodynamic sound converter in conformity with the intensity of the magnetization of the coil is switched on and off in such a way that a sound converter is switched on when the magnetization has reached a predetermined value, and is switched off as soon as the magnetization drops below another predetermined value.

7 Claims, 2 Drawing Figures

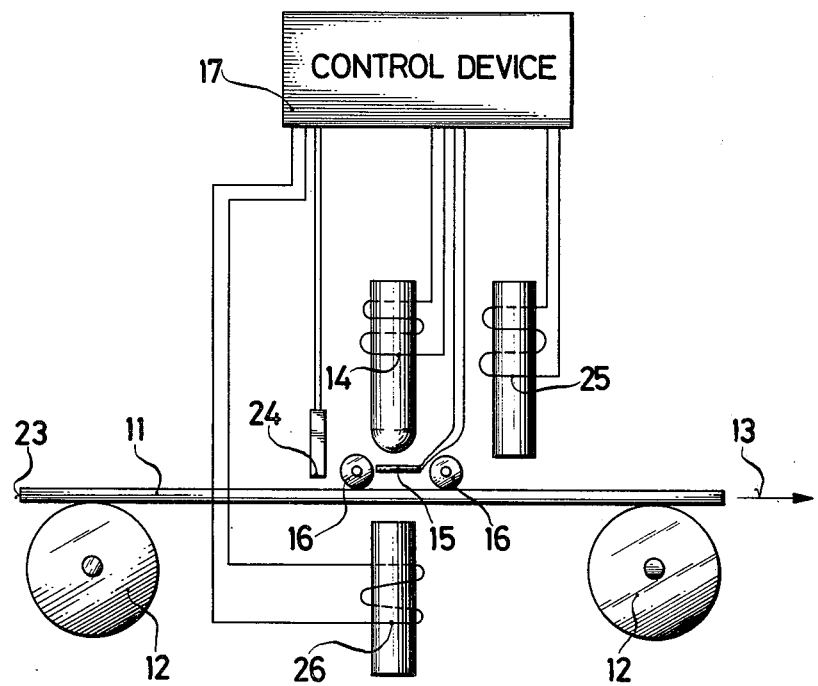
FIG. 1
FIG. 2
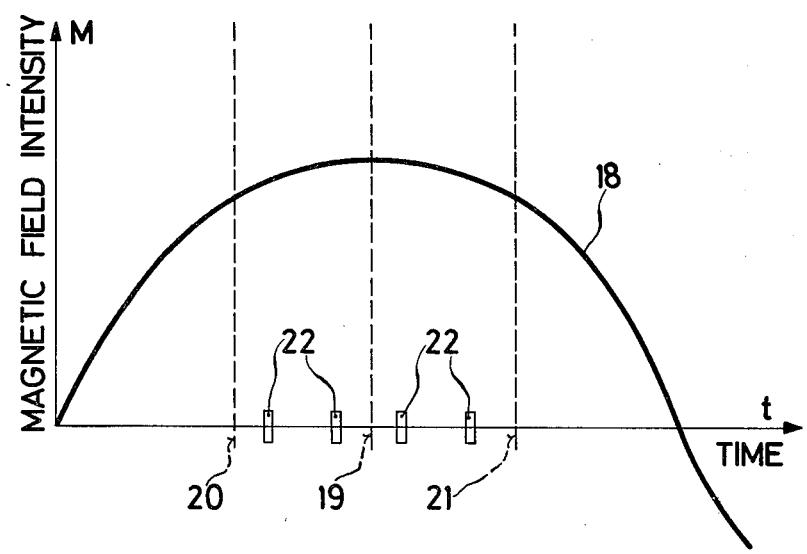

METHOD OF AND DEVICE FOR MATERIAL CHECKING BY ULTRA SOUND WHILE EMPLOYING AN ELECTRODYNAMIC SOUND CONVERTER

The present invention relates to a method of and device for material testing by ultra sound without destroying the material while utilizing an electrodynamic sound converter according to which the workpiece is, when being checked, passed in front of the testing device in an uninterrupted movement.

A method of this type is required in many instances, for instance when checking metal sheets in a rolling mill or when testing the welding seam while building up pipelines. Particularly in the first mentioned instance caused by the high rolling speed, also a high testing speed is realized.

With heretofore known electrodynamic sound converters, the force of attraction of the strong magnetic field between sound converter and workpiece impedes the movement of the workpiece. In particular at the workpiece edges, high forces of attraction occur, and as a rule, the current has to be turned off when it is intended to advance the workpiece. The magnetic field causes a deep magnetic track which during the further processing interferes and can be eliminated only be relatively large demagnetizing devices. The demagnetization requires considerable time because the magnetism is rather deeply located in the interior of the workpiece. It is for this reason that the heretofore known electrodynamic sound converters are unsuitable in connection with the testing at high testing speeds and with an uninterrupted movement of the workpiece. By means of these dynamic sound converters, the workpiece can only be checked by steps and sections, while requiring considerable time.

It is, therefore, an object of the present invention to provide a method and device for testing workpieces without destroying them, by means of an electrodynamic converter according to which the workpiece moves in an uninterrupted manner and at high speed in front and past the testing or checking head during the testing operation. The testing is carried out over overlapping sections while also in an inverse manner the testing head can move and the workpiece may be kept standing still. The residual magnetism remaining after the test in the workpiece will be negligible, and furthermore the force of attraction exerted upon the workpiece of the coil generating the magnetic field will be considerably less than heretofore.

These and other objects and advantages of the invention will appear more clearly from the following specification in connection with the accompanying drawings, in which:

FIG. 1 illustrates a device according to the invention for practicing the method according to the invention.

FIG. 2 is a graph showing the relationship between the test intervals and the magnetizing strength.

The method according to the present invention is characterized primarily in that the coil for generating the magnetic field is energized by an alternating current or by an intermittant or alternating direct current, and in that the testing device is in conformity with the strength of the magnetization of the coil turned on and turned off in such a way that the testing device is turned on when the magnetization has reached a predetermined value, and is turned off as soon as the strength of the magnetization drops below a predetermined value. In this way the testing device can be synchronized with the energizing current of the coil by turning the high frequency coil on and off. The synchronization may, however, also be effected with always turned on high frequency energization by turning on and off the indicating device of the testing device. The turning on and off by means of suitable circuits can be directly coupled to a predetermined height or intensity of the energizing current. However, a control can also be effected by the zero passages of the energizing current with built-in-time delay, whenever a single frequency is employed for the energizing current of the coil. By means of synchronization it will be obtained that the test is effected only when the magentic field strength is in the vicinity of its maximum where it changes timewise only slightly and changes as to strength only insignificantly. In the zero passages and in the vicinity thereof, the checking is suppressed so that always a faulty indication occurs which is independent of the strength of the magnetic field. In view of the synchronization it is possible to employ an alternating current of such high frequency for the energization of the coil that the magnetic field only insignificantly enters the interior of the workpiece in spite of the high field strength on the workpiece surface. For the ultrasonic generation, however, only the magnetic field on the workpiece surface is needed and used.

The magnetism in the interior of the workpiece does not contribute anything to the ultrasonic generation. This magnetism entering the interior, however, to a considerable extent determines the interfering force of attraction between the testing device and the workpiece. This interfering force of attraction already during the energization of the coil can be considerably reduced by the cyclic alternating current of 50 Hz. (50 cycles frequency) in Germany corresponding to 60 Hz (60 cycles frequency in the USA)

Only by reducing the force of attraction, it has become possible to move the workpiece in an uninterrupted movement also with its edge in front of and past said testing head without damaging the testing head by the force of attraction.

A further advantage obtained by the present invention consists in that the workpiece becomes magnetic only in a near region at the surface. This magnetism must as a rule be eliminated by demagnetizing because it interferes with the further processing. The magnetism located at the surface can be eliminated in fractions of a second by the customary demagnetizing methods, whereas the magnetism remaining deep in the workpiece as it is generated with customary electrodynamic converters, in order to be eliminated requires a plurality of seconds so that the flow of production is already impeded by the time required for demagnetizing in rolling mills. For the demagnetization according to the invention, no particular device is necessary; it is effected rather automatically when the workpiece moves out the magentic field of the coil of the electrodynamic sound converter, because the magnetic field is an alternating field, and it decreases currently with the distance from the coil. A device for carrying out the method becomes particularly simple when the coil for generating the magnetic field is energized by the alternating current of 50 Hz to 60 Hz.

The force of attraction between testing device and workpiece, which force interferes particularly at the workpiece edge, is furthermore reduced by the fact that in the device there is built in a feeler for recognizing the workpiece edge, by which feeler, when the workpiece edge is reached, the current intensity of the coil of the testing device is reduced or completely turned off.

A further reduction in the force of attraction between the testing device and the workpiece at the workpiece edge is realized by the fact that the said feeler, when reaching the workpiece edge, turns on a second coil. The second coil, when viewing in the direction of movement of the workpiece, is located behind the coil for the magnetic field. This second coil is energized by alternating current, and its current intensity for the energization drops after a short period to zero. At the same time when said second coil is turned on, the coil of the testing device is turned off, or its energization is greatly reduced. The coil is turned on fully only when the feeler senses the approach of the next workpiece to be checked. The second coil thus takes over the demagnetization of the workpiece edge. When the second coil is turned on, it is first located above the workpiece. Its current of energization is already considerably reduced and approaches zero as soon as the workpiece edge during the further advance of the workpiece is located precisely below the second coil. In this way, the second coil can completely demagnetize the workpiece edge without the full force of attraction becoming effective by the said second coil and the workpiece edge. Such full force of attraction would occur with the maximum current of energization of said coil when the workpiece edge moves away from said coil.

When checking thin metal sheets, the above described devices are not sufficient for reducing the force of attraction between the sheet and the testing device, in order to prevent the sheet from hitting the testing head. Therefore, according to a further development of the present invention it is provided that on that side of the workpiece which is located opposite the testing head there are arranged one or more coils energized by alternating current, which coils generate a counterforce to the magnetic force exerted by the testing or checking head upon the workpiece.

Referring now to the drawing in detail, the metal sheet 11 to be tested moves, according to FIG. 1, on the rollers 12 of a roller train in the direction 13. Above said roller train there is provided the electrodynamic sound converter. This converter comprises a coil 14 for generating the magnetic field, and furthermore comprises a high frequency coil 15 for generating high frequency eddy currents in the sheet 11 to be checked, whereby in a manner known per se, due to the Lorentz forces ultrasonic waves are generated in the sheet 11. The electrodynamic sound converter is in a floating manner arranged slightly spaced from and above the sheet 11 so as not to contact the latter. However, for securing the slight distance between the sound converter and the sheet 11, supporting rollers 16 may additionally be arranged on said electrodynamic sound converter. The coils 14 and 15 of the electrodynamic sound converter are through conductors connected to a central control device 17. This control device 17 controls the energizing current by the coil 14 which energizing current in conformity with the invention is an intermittant direct current or an alternating current. The control device 17 furthermore in conformity with the strength of the magnetization of coil 14 acts upon the high-frequency coil 15 with a high-frequency current in conformity with the frequency of the ultra sound. It is particularly advantageous when the high frequency current coil 15 is turned on only when, in conformity with FIG. 2, the magnetizing curve 18 of coil 14 has almost reached its maximum value located at 19. The turning on of the high frequency coil 15 according to FIG. 2 therefore is effected at 20 and ends at 21. Between 20 and 21 there is only a very slight change in the magnetization of coil 14.

The change in the magnetization in this region is particularly small when the core of the coil is saturated in the entire region. In this region between 20 and 21 there is so much time available that a plurality of testing pulses designated in FIG. 2 with the numeral 22 can be introduced. These testing pulses may also have a different frequency. The generation of the synchronization between the energizing current of coil 14 and the current of the high frequency coil 15 as well as the generation of the testing pulses 22 is effected in the control device 17 by means of customary circuits well known to anybody skilled in the art.

When the edge 23 at the end of the sheet 11 during the passage direction 13 reaches the sensor 24, this information is conveyed to the central control device 17. The sensor 24 may consist of a small magnet which strengthened reinforced, amplified or enhanced by the edge 23 of the sheet 11 is pulled in the direction 13 whereby an electrical contact will be actuated. When the sensor 24 responds, the following operations will be controlled by the central control device 17.

1. The current for the coil 14 is decreased with such time delay or turned off completely that while the edge 23 is still checked ultrasonically, a removing of the edge 23 from the coil at full energization will be avoided.

2. When the current is turned on for the demagnetizing coil 25, this current decreases currently and reaches only an insignificant intensity when the edge 23 leaves the demagnetizing coil 25. As soon as this occurs, the current for the coil 14 is fully turned on again, and the demagnetizing coil 25 is completely turned off.

The removal of the edge 23 from the demagnetizing coil 25 may be indicated on the control device 17 by a non-illustrated sensor. However, the removal of the edge 23 can be fixed also without sensor purely in a timewise manner when the advancing speed of the sheet 11 is always the same. In particular when checking very thin sheets, it may be advantageous for preventing the sheet from bending in view of the magnetic force of coil 14, when a coil 26 is arranged opposite the coil 14. The coil 26 is energized with the same current which passes through coil 14 whereby always a counterforce will be generated to counter the magnetic force of attraction of coil 14.

It is, of course, to be understood that the present invention is by no means, limited to the specific showing in the drawing, but also comprises any modifications within the scope of the appended claims.

What we claim is:

1. A method of ultrasonically checking a moving workpiece utilizing an electrodynamic sound converter which includes an electromagnetic coil means for creating a magnetic field when energized and a high frequency coil for testing the workpiece magnetized by said electromagnetic coil means when energized by a current of varying amplitude, said method comprising: initiating operation of a control device when the amplitude of the current to said electromagnetic coil means reaches a given value to turn on energization of said high frequency coil for testing said workpiece and terminating operation of said high frequency coil when said amplitude falls below a given value.

2. A method in combination according to claim 1, which includes the step of energizing said coil means by an alternating current of from 50 to 60 Hz.

3. A method in combination according to claim 1, which includes the step of reducing the current intensity of said coil means when the edge of a workpiece reaches the proximity of said high frequency coil.

4. An apparatus for ultrasonically checking a moving workpiece comprising: an electrodynamic sound converter having an electromagnetic coil means for creating a magnetic field when energized and a high frequency coil for testing the workpiece magnetized by said electromagnetic coil means when energized by a current of varying magnitude, and a control device connected to said electromagnetic coil means and said high frequency coil, said electromagnetic coil means initiating operation of said control device when the amplitude of the current to said electromagnetic coil means reaches a given value to turn on energization of said high frequency coil for testing said workpiece and to terminate operation of said high frequency coil when said amplitude falls below a given value.

5. A device in combination according to claim 4, which includes a second coil forming a customary demagnetizing coil and located behind said first coil when viewing the relative movement of the workpiece with regard to said first coil, said second coil being electrically connected to said control device and being adapted to be switched on by said control device in response to a workpiece edge reaching the proximity of said first coil.

6. A device in combination according to claim 4, which includes at least one third coil arranged opposite and in spaced relationship to said first coil and electrically connected to said control device, said at least one third coil being energizable by alternating current controlled by said control device for generating a counter force acting upon a workpiece passing between said first and third coil and counteracting the magnetic force of attraction exerted by said first coil upon a workpiece passing between said first and third coil.

7. An apparatus as claimed in claim 4, in which a detector connected to said control device is placed adjacent said workpiece ahead of said sound converter, said detector sensing the end of a workpiece and initiating operation of said control device to reduce the current in said electromagnetic coil means and thereby decrease the magnetization of the end of said workpiece.

* * * * *